US00PP32492P3

(12) United States Plant Patent
Beckman

(10) Patent No.: US PP32,492 P3
(45) Date of Patent: Nov. 17, 2020

(54) CALLA LILY PLANT NAMED 'DIVA SIBERIA'

(50) Latin Name: *Zantedeschia aethiopica*
Varietal Denomination: Diva Siberia

(71) Applicant: Dümmen Group B.V., De Lier (NL)

(72) Inventor: Peter Beckman, Santa Cruz, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,429

(22) Filed: Oct. 2, 2019

(65) Prior Publication Data

US 2020/0113110 P1 Apr. 9, 2020

Related U.S. Application Data

(60) Provisional application No. 62/766,213, filed on Oct. 5, 2018.

(51) Int. Cl.
*A01H 5/02* (2018.01)
*A01H 6/56* (2018.01)

(52) U.S. Cl.
USPC ..... Plt./490
CPC ..... *A01H 6/56* (2018.05)

(58) Field of Classification Search
USPC ..... Plt./490
CPC ..... A01H 5/002
See application file for complete search history.

*Primary Examiner* — Annette H Para
(74) *Attorney, Agent, or Firm* — The Webb Law Firm

(57) ABSTRACT

'Diva Siberia' is a new variety of calla lily plant having white colored spathes. The leaves are green with no maculations present.

1 Drawing Sheet

Botanical classification: *Zantedeschia aethiopica.*
Varietal denomination: 'Diva Siberia'.

BACKGROUND OF THE NEW PLANT

The present invention comprises a new and distinct cultivar of calla lily, botanically known as *Zantedeschia aethiopica* and hereinafter referred to by the cultivar name 'Diva Siberia'.

'Diva Siberia' is a product of a planned breeding program and the new cultivar was selected in Santa Cruz, Calif. from the F2 population of the crossing of unpatented *Zantedeschia* seedling 7037-07 (female parent) with unpatented *Zantedeschia* seedling 95104 (male parent). When compared to its female parent, the blooms of 'Diva Siberia' are more white in color, more abundant, and exhibit earlier maturity. Further, the foliage canopy is more dense and compact. Its disease resistance is more superior to its female parent and its flower stems are slimmer and stronger. When compared to its male parent, the blooms and overall plant size of 'Diva Siberia' are larger.

The new variety was initially asexually reproduced through tissue culture propagation in Santa Cruz, Calif. Asexual reproductions of 'Diva Siberia' have demonstrated that the combination of characteristics as herein disclosed for the new variety are retained and reproduced true to type through successive generations of asexual reproduction.

Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Diva Siberia' which, in combination, distinguish this calla lily as a new and distinct cultivar:

1. White colored spathes; and
2. Leaf maculations absent.

Table 1 provides a comparison of 'Diva Siberia' to similar *Zantedeschia aethiopica* varieties 'A405' (U.S. plant patent pending), 'Colombe de la Paix' (unpatented), 'Avalanche' (unpatented), and 'Innocence' (unpatented). Further, 'Diva Siberia' flowers one week earlier than 'Innocence' and is more productive.

TABLE 1

| Comparison variety | Differing trait(s) | Comparison expression | Present variety expression |
|---|---|---|---|
| 'A405' | Plant height | 30-40 cm | 50-120 cm |
| 'Colombe de la Paix' | Plant height | 60-150 cm | 50-120 cm |
| 'Avalanche' | Leaf maculations | Present | Not present |
| 'Innocence' | Spathe color | White Group RHS 155B | Between White Group RHS 155C and 155D |

BRIEF DESCRIPTION OF THE DRAWING

The accompanying photographic drawing illustrates the new variety, with the colors being as nearly true as is possible with color illustrations of this type.

DESCRIPTION OF THE NEW PLANT

Type: Evergreen.
Main use: Cut flower.
Form: Upright and semi-spreading.

Height of leaf canopy above the soil: 70-100 cm.
Height of top of inflorescences above the soil: 80-120 cm.
Number of inflorescences per tuber: 18-20 cm in diameter: 4-6.
Lastingness of inflorescences on the plant: 14-28 days.
Disease/pest resistance: Strong tolerance to *Pythium* root rot and other root pathogens.
Root color: White.
Berries: None present.
Leaves:
*Width*.—15-20 cm.
*Length*.—25-40 cm.
*Shape*.—Sagittate.
*Apex*.—Apiculate.
*Base*.—Sagittate.
*Margin*.—Entire.
*Color*.—Upper surface: Green Group RHS 137A, with no maculations present. Lower surface: Green Group RHS 137C, with no maculations present.
*Surface texture*.—Smooth (both surfaces).
*Leaf venation*.—None/indistinct.
*Petiole*.—Length: 35-80 cm. Diameter: 1.2-2 cm. Texture: Smooth. Shape: Slim columnar Color: The base is Green Group RHS 137B and the upper portion is Green Group RHS 137C.
Spathe:
*Length*.—15-20 cm.
*Width*.—10-15 cm.
*Height*.—15-20 cm.
*Fragrance*.—Moderately sweet.
*Shape*.—Funnel.
*Texture*.—Smooth.
*Apex*.—Pointed.
*Base*.—Continuous.
*Margin*.—Entire, with slight undulation present.
*Throat spot*.—Absent.
*Color*.—Between White Group RHS 155C and 155D (upper and lower surfaces).
Spadix:
*Length*.—7-14 cm.
*Diameter*.—0.5-0.8 cm.
*Color*.—Yellow Group RHS 13A to 13B.
*Position relative to spathe*.—Upright from base.
*Apex*.—Apiculate.
*Location of female organs*.—Upper portion of spadix.
*Location of male organs*.—Lower portion of spadix.
*Pistil number*.—Numerous, more than 20.
*Pollen color*.—White Group RHS 155A to 155B.
*Peduncle color*.—Green Group RHS 137A to Yellow-Green Group RHS 144A.

I claim:

1. A new and distinct variety of calla lily plant named 'Diva Siberia' as herein described and illustrated.

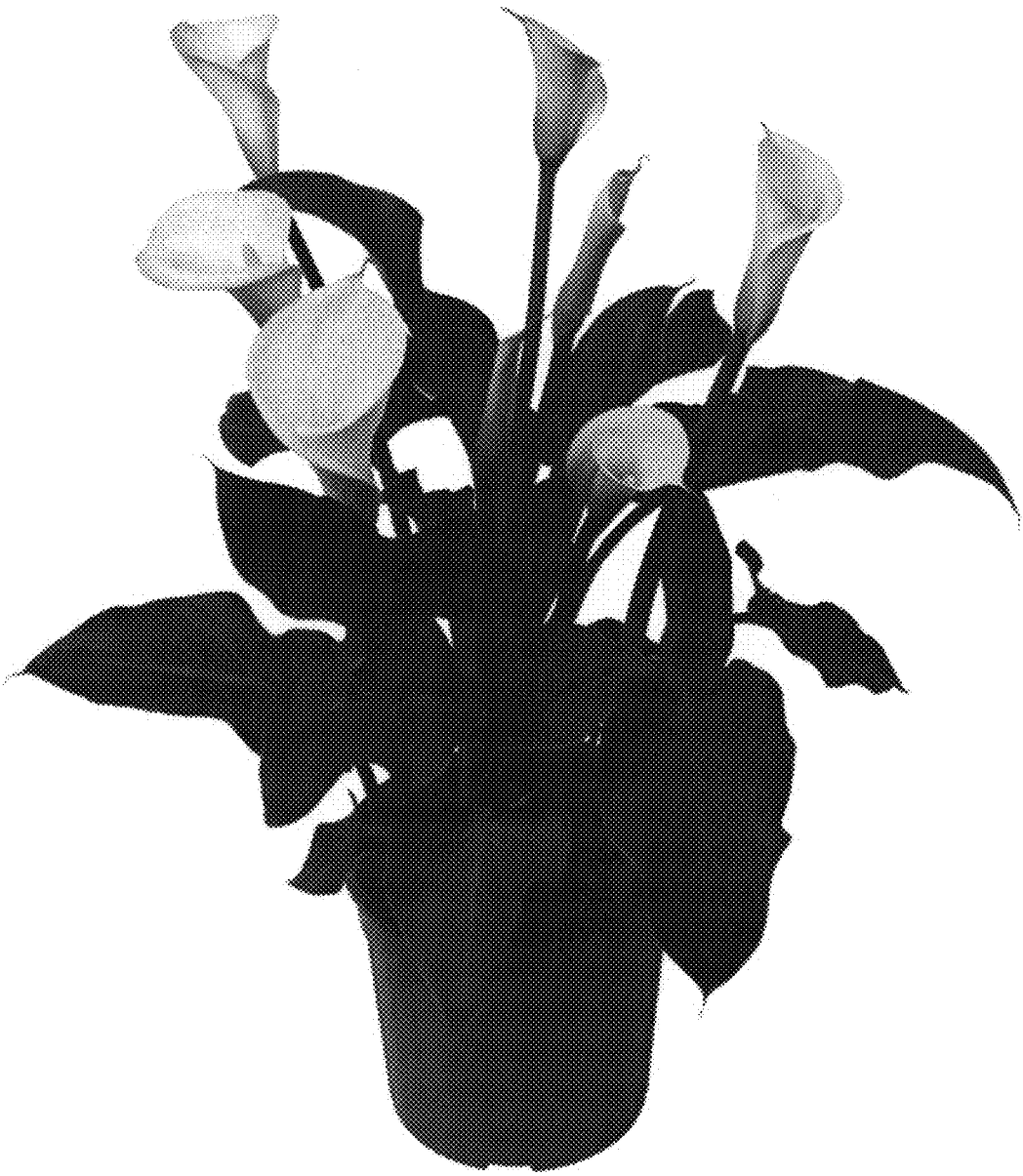

* * * * *